United States Patent [19]
Dubief et al.

[11] Patent Number: 5,650,383
[45] Date of Patent: Jul. 22, 1997

[54] COMPOSITION FOR WASHING AND/OR CONDITIONING KERATINOUS MATTER, CONTAINING A SILICONE AND AN AMPHOTERIC POLYMER DERIVED FROM DIALLYDIALKYLAMMONIUM AND FROM AN ANIONIC MONOMER

[75] Inventors: Claude Dubief, Le Chesnay; Daniele Cauwet, Paris, both of France

[73] Assignee: L'Oreal, Paris, France

[21] Appl. No.: 428,394

[22] Filed: Apr. 25, 1995

Related U.S. Application Data

[63] Continuation of Ser. No. 900,562, Jun. 18, 1992, abandoned.

[30] Foreign Application Priority Data

Jun. 21, 1991 [FR] France .................. 9107677

[51] Int. Cl.$^6$ .................. C11D 3/37; C11D 1/02; C11D 1/66; C11D 1/88

[52] U.S. Cl. .................. 510/122; 510/123; 510/124; 510/125; 510/126; 510/127; 510/128; 510/421; 510/426; 510/433; 510/466; 510/475; 510/490; 510/492; 510/499; 424/70.12; 424/70.17

[58] Field of Search .................. 252/174.15, 547, 252/548, DIG. 13, 174.25; 510/122, 123, 124, 125, 126, 127, 128, 421, 426, 433, 475, 490, 492, 499, 466; 424/70.12, 70.17

[56] References Cited

U.S. PATENT DOCUMENTS

| | | | |
|---|---|---|---|
| 4,741,855 | 5/1988 | Grote et al. | 252/142 |
| 4,764,365 | 8/1988 | Boothe et al. | 424/81 |
| 4,772,462 | 9/1988 | Boothe et al. | 424/70 |
| 4,788,006 | 11/1988 | Bolich, Jr. et al. | 252/550 |
| 5,034,218 | 7/1991 | Duvel | 424/70 |
| 5,077,042 | 12/1991 | Darkwa et al. | 424/71 |
| 5,085,857 | 2/1992 | Reid et al. | 424/70 |
| 5,152,914 | 10/1992 | Forster et al. | 252/174 |
| 5,180,584 | 1/1993 | Sebag et al. | 424/401 |
| 5,194,260 | 3/1993 | Grollier et al. | 424/401 |
| 5,275,755 | 1/1994 | Sebag et al. | 252/174.15 |
| 5,293,885 | 3/1994 | Darkwa et al. | 132/209 |
| 5,376,364 | 12/1994 | Darkwa et al. | 424/70.2 |
| 5,393,305 | 2/1995 | Cohen et al. | 8/406 |

FOREIGN PATENT DOCUMENTS

| | | |
|---|---|---|
| 401867 | 11/1984 | European Pat. Off. . |
| 203750 | 5/1986 | European Pat. Off. . |
| 269243 | 10/1987 | European Pat. Off. . |
| 392320 | 4/1990 | European Pat. Off. . |
| 2548019 | 6/1984 | France . |
| 2058103 | 8/1980 | United Kingdom . |

*Primary Examiner*—Michael P. Tierney
*Attorney, Agent, or Firm*—Brumbaugh, Graves, Donohue & Raymond

[57] ABSTRACT

Composition for washing and/or conditioning keratinous matter, containing a silicone and an amphoteric polymer derived from diallyldialkylammonium and from an anionic monomer.

Composition for washing and/or conditioning keratinous matter, characterised in that it contains, in an aqueous medium, a surface-active agent possessing detergent properties, at least one silicone which is insoluble in the medium and at least one copolymer derived from diallyldialkylammonium and from an anionic monomer.

17 Claims, No Drawings

COMPOSITION FOR WASHING AND/OR CONDITIONING KERATINOUS MATTER, CONTAINING A SILICONE AND AN AMPHOTERIC POLYMER DERIVED FROM DIALLYDIALKYLAMMONIUM AND FROM AN ANIONIC MONOMER

This application is a continuation of application Ser. No. 07/900,562, filed on Jun. 18, 1992 now abandoned.

The present invention relates to compositions for washing and/or conditioning keratinous matter and more particularly hair, containing a silicone and an amphoteric polymer derived from diallyldialkylammonium and from an anionic monomer, and to the processes for treatment of keratinous matter using such compositions.

It is well known that hair is sensitised or made brittle to various degrees by the action of atmospheric agents and by the action of various cosmetic treatments such as permanent waving, straightening, dyeing or bleaching treatments. The hair then becomes difficult to disentangle and to style. In addition, it becomes rough in feel.

Silicones which contribute softness, shine, lightness and which can make disentangling easier have already been employed in washing compositions.

Use has also already been made in the past, in hair treatment compositions, of amphoteric polymers such as, for example, octylacrylammide/acrylate/butylaminoethyl methacrylate copolymers, $C_1$–$C_{18}$ alkyl methacrylate/carboxymethyldimethylammoniomethyl methacrylate copolymers or chitosan derivatives.

The Applicant has found surprisingly that by using, in a composition for treatment of keratinous matter, a silicone in combination with a copolymer derived from diallyldialkylammonium and from an anionic monomer, and more particularly acrylic acid, it is possible, when it is applied in particular to hair, to obtain excellent disentangling and softness properties when compared with hair treated with compositions containing only the silicone or the amphoteric polymer by itself.

Hair treated in this way is particularly easy to disentangle, soft and light. Moreover, it is well-behaved, is easy to style and has more body; this effect is particularly advantageous when the hair is damaged or sensitised or in the treatment of fine hair.

The subject of the invention therefore consists of a composition for treatment of keratinous matter, containing at least one silicone and an amphoteric polymer derived from diallyldialkylammonium and from an anionic monomer.

Another subject of the invention consists of a process for treatment of keratinous matter using such a composition.

A further subject of the invention is the use of the combination of a polymer derived from diallyldialkylammonium and from an anionic monomer and of silicones for the treatment of keratinous matter and in particular for endowing hair with improved softness and disentangling properties.

Other subjects of the invention will emerge on reading the description and the examples which follow.

The compositions for washing and conditioning keratinous matter, in accordance with the invention, are essentially characterised in that they contain, in an aqueous medium:

at least one surface-active agent possessing detergent properties;

at least one silicone which is insoluble in this medium; and at least one copolymer of diallyldialkylammonium and of an anionic monomer.

The surface-active agents employed in the washing and conditioning compositions in accordance with the invention are known per se and are chosen from anionic, amphoteric, zwitterionic and nonionic surface-active agents or mixtures thereof, which have detergent properties.

Among the anionic surface-active agents there may be mentioned the alkali metal salts, the ammonium salts, the amine salts, the aminoalcohol salts and the magnesium salts of the following compounds: alkyl ether sulphates, alkylamidoether sulphates, alkylarylpolyether sulphates, monoglyceride sulphates, alkylsulphonates, alkylamide sulphonates, alkylarylsulphonates, olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl ether phosphates, acylsarcosinates and N-acyltaurates.

The alkyl or acyl radical of these various compounds generally consists of a carbon chain containing from 12 to 20 carbon atoms.

Among the anionic surface-active agents there may also be mentioned the salts of fatty acids such as the salts of oleic, ricinoleic, palmitic and stearic acids, copra oil or hydrogenated copra oil acids, and acyllactylates in which the acyl radical contains from 8 to 20 carbon atoms.

It is also possible to employ weakly anionic surface-active agents such as polyoxyalkylenated carboxylic ether acids, in particular those containing 2 to 50 ethylene oxide groups.

The nonionic surface-active agents are chosen more particularly from the polyethoxylated, polypropoxylated or polyglycerolated alcohols or α-diols or alkylphenols or fatty acids, with a fatty chain containing 8 to 18 carbon atoms, the number of ethylene oxide or propylene oxide groups being between 2 and 50 and the number of glycerol groups being between 2 and 30.

There may also be mentioned the copolymers of ethylene and propylene oxides, condensates of ethylene and propylene oxides with fatty alcohols, polyethoxylated fatty amides preferably containing 2 to 30 moles of ethylene oxide, polyglycerolated fatty amides preferably containing 1 to 5, and in particular 1.5 to 4, glycerol groups, polyethoxylated fatty amines preferably containing 2 to 30 moles of ethylene oxide, oxyethylenated sorbitan fatty acid esters preferably containing 2 to 30 moles of ethylene oxide, sucrose fatty acid esters, polyethylene glycol fatty acid esters, glycol fatty acid esters, alkylpolyglycosides, amine oxides such as $C_{10}$–$C_{14}$-alkylamine oxides or N-acylamidopropylmorpholine oxides.

The preferred amphoteric or zwitterionic surface-active agents are the derivatives of aliphatic secondary or tertiary amines in which the aliphatic radical is a linear or branched chain containing 8 to 18 carbon atoms and which contains at least one water-solubilising carboxylate, sulphonate, sulphate, phosphate or phosphonate anionic group, $C_8$–$C_{20}$-alkylbetaines, sulphobetaines, $C_8$–$C_{20}$-alkylamido-$C_1$–$C_6$-alkylbetaines or $C_8$–$C_{20}$-alkylamido-$C_1$–$C_6$-alkylbetaines.

Among the amine derivatives there may be mentioned the products sold under the name Miranol, as described in U.S. Pat. Nos. 2,528,378 and 2,781,354 and classified in the CTFA dictionary, 3rd edition, 1982, under the names of Amphocarboxyglycinates and Amphocarboxypropionates.

The surface-active agents are employed in the compositions in accordance with the invention in sufficient proportions to impart a detergent character to the composition and are preferably between 5 and 50% by weight relative to the total weight of the composition, and in particular between 8 and 35%.

The silicones employed in accordance with the present invention are polyorganosiloxanes which are insoluble in aqueous media, which may take the form of oils, waxes, gums or resins.

The organopolysiloxanes are defined in greater detail in the work by Walter Noll "Chemistry and Technology of Silicones" (1968), Academic Press.

The polysiloxanes employed in accordance with the invention are chosen from volatile silicones which have a boiling point of between 60° C. and 260° C. or else nonvolatile silicones chosen in particular from polyalkylsiloxanes, polyarylsiloxanes, polyalkylarylsiloxanes, silicone gums and resins, organomodified polysiloxanes and mixtures thereof.

The volatile silicones may be chosen from:

(i) cyclic silicones containing from 3 to 7 silicon atoms and preferably 4 to 5. These are, for example, the octamethylcyclotetrasiloxane sold under the name of Volatile Silicone 7207 by Union Carbide or Silbione 70045 V 2 by Rhône Poulenc, the decamethylcyclopentasiloxane sold under the name of Volatile Silicone 7158 by Union Carbide, Silbione 70045 V 5 by Rhône Poulenc and mixtures thereof.

Cyclocopolymers of the dimethylsiloxane/methylalkylsiloxane type may also be mentioned, such as Silicone Volatile FZ 3109 sold by the company Union Carbide, which is a dimethylsiloxane/methyloctylsiloxane cyclopolymer.

Furthermore, it is possible to employ mixtures of cyclic silicones with organic compounds derived from silicon, such as the mixture of octamethylcyclotetrasiloxane and tetratrimethylsilylpentaerythritol (50/50) and the mixture of octamethylcyclotetrasiloxane and 1,1'-oxy-(2,2,2',2',3,3'-hexatrimethylsilyloxy)bisneopentane;

(ii) the linear volatile silicones containing 2 to 9 silicon atoms and having a viscosity lower than or equal to $5\times10^{-6}$ m$^2$/s at 25° C. These are, for example, the hexamethyldisiloxane sold under the name Silbione 70 041 V 0.65 by the company Rhône Poulenc, the decamethyl-tetrasiloxane sold under the name SH 200 by the company Toray Silicone or the volatile polymethylphenylsiloxanes such as the product Siliconol AS sold by the company Wacker. The silicones forming part of this class are also described in the article published in Cosmetics and toiletries, Vol. 91, Jan. 1976, p. 27–32, Todd & Byers "Volatile Silicone fluids for cosmetics".

The nonvolatile silicones are chosen especially from polyalkylsiloxanes. Mention may be made chiefly of linear polydimethylsiloxanes containing trimethylsilyl end groups with a viscosity of $5\times10^{-6}$ to 2.5 m$^2$/s at 25° C. and preferably $10^{-5}$ to 1 m$^2$/s, for example and without any limitation being implied:

the Silbione oils of the series 47 and 70 047 marketed by Rhône Poulenc, such as the oil 47 V 500,000, the oils of the series 200 from the company Dow Corning, the Viscasil oils from General Electric and certain oils from the SF series from General Electric (SF 96, SF 18).

Linear polydimethylsiloxanes containing dimethylsilanol end groups are also mentioned, such as the oils of the series 48 from Rhône Poulenc.

In this class of polyalkylsiloxanes it is also possible to mention polyalkylsiloxane waxes sold by the company Goldschmidt under the names Abil Wax 9800 and Abil Wax 9801, which are poly-$C_1$–$C_{20}$-alkylsiloxanes.

Among the polyalkylarylsiloxanes there may be mentioned polydimethylmethylphenylsiloxanes, polymethylphenylsiloxanes and polydimethyldiphenylsiloxanes which are linear and/or branched, with a viscosity of $10^{-5}$ to $5\times10^{-2}$ m$^2$/s at 25° C., such as, for example:

the oils of the series Rhodorsil 70 633 and 763 from Rhône Poulenc, the Silbione oils of the series 70 641 from Rhône Poulenc, the oil DC 556 Cosmetic Grad Fluid from Dow Corning, the silicones of the PK series from Bayer, such as PK20, the silicones of the PN and PH series from Bayer, such as PN 1000 and PH 1000, some oils of the SF series from General Electric, such as SF 1250, SF 1265, SF 1154 and SF 1023.

The silicone gums in accordance with the present invention are polydiorganosiloxanes of high molecular masses of between 200,000 and 1,000,000, employed by themselves or as a mixture in a solvent chosen from volatile silicones such as defined above, polydimethylsiloxane (PDMS) oils, polyphenylmethylsiloxane (PPMS) oils, isoparaffins, methylene chloride, pentane, dodecane, tridecane, tetradecane or mixtures thereof.

For example, the following gums are mentioned:

poly[(dimethylsiloxane)/(methylvinylsiloxane)], poly[(dimethylsiloxane)/(diphenylsiloxane)], poly[(dimethylsiloxane)/(phenylmethylsiloxane)], poly[(dimethylsiloxane)/(diphenylsiloxane)/-(methylvinylsiloxane)].

For example, the following mixtures may be mentioned without any limitation being implied:

the mixtures made up from a polydimethylsiloxane hydroxylated at the end of a chain (Dimethiconol according to the CTFA nomenclature) and a cyclic polydimethylsiloxane (Cyclomethicone according to CTFA nomenclature), such as the product Q 2 1401 sold by the company Dow Corning, the mixtures made up from a polydimethylsiloxane gum with a cyclic silicone, such as the product SF 1214 Silicone Fluid from the company General Electric (which has an SE 30 gum, corresponding to a dimethicone, which has a molecular weight of 500,000, dissolved in the silicone SF 1202 Silicone Fluid (corresponding to decamethylcyclopentasiloxane)), mixtures of two PDMSs of different viscosities, especially of a PDMS gum and of a PDMS oil, such as the products SF 1236 and CF 1241 from the company General Electric. The product SF 1236 is the mixture of an SE 30 gum defined above, with a viscosity of 20 m$^2$/s and of an SF 96 oil with a viscosity of $5\times10^{-6}$ m$^2$/s (15% of SE 30 gum and 85% of SF 96 oil).

The product CF 1241 is the mixture of an SE 30 gum (33%) and of a PDMS (67%) with a viscosity of $10^{-3}$ m$^2$/s.

The organopolysiloxane resins which can be employed in accordance with the invention are cross-linked siloxane systems containing the units R'$_2$SiO$_{2/2}$, R'SiO$_{3/2}$ and SiO$_{4/2}$, in which R' denotes a hydrocarbon group containing 1 to 6 carbon atoms or a phenyl group. Among these products those particularly preferred are ones in which R' denotes a lower alkyl radical or a phenyl radical.

Among these resins there may be mentioned the product sold under the name Dow Corning 593 or those sold under the names Silicone Fluid SS 4230 and SS 4267 by the company General Electric and which are "dimethyl/trimethylpolysiloxanes".

The organomodified silicones are silicones defined above and whose structure includes one or more organofunctional groups directly attached to the siloxane chain or attached via a hydrocarbon radical.

Among these organomodified silicones there may be mentioned, for example, the silicones containing:

1—polyethyleneoxy and/or polypropyleneoxy groups optionally containing alkyl groups, such as:

the product called dimethicone copolyol sold by the company Dow Corning under the names DC 1248, and the $C_{12}$-alkyl methicone copolyol sold by the company Dow Corning under the name Q2 5200.

the Silwet oils L 722, L 7500, L 77 and L 711 from the company Union Carbide, the mixture of dimethicone copolyol and of cyclomethicone, such as the product sold under the name Q2—3225C by the company Dow Corning.

2—substituted or unsubstituted amine groups such as the products sold under the name GP4 Silicone Fluid and GP 7100 by the company Genesee or the products sold under the names Q2 8220, X2 8200 and DC 929 or Q2 7224 by the company Dow Corning. The substituted amine groups are in particular $C_1$–$C_4$-alkylamino groups, 3—thiol groups, as in GP 72 A and GP 71 from Genesee or in the product SLM 50253/5 from the company Wacker, 4—carboxylate groups as in the products described in Patent EP-A-186,507 of the company Chisso Corporation, 5—alkoxy groups, such as the products sold under the name Silicone Copolymer F-755 by SWS Silicones, and Abil Wax 2428, 2434 and 2440 by the company Goldschmidt, 6—hydroxyl groups, such as the polyorganosiloxanes containing a hydroxyalkyl functional group, which are described in French Patent Application No. FR-85/16,334.

The product 71615 V 300 sold by the company Rhône Poulenc is mentioned as an example.

7—acyloxyalkyl groups, such as, for example, the polyorganosiloxanes described in Patent Application FR-A-2,641,185, 8—artionic groups of carboxylic type such as the alkylcarboxylic groups such as those present in the product X-22-3701E from the company Shin-Etsu or in the product Silicone Fluid FZ 3703 from the company Union Carbide, 2-hydroxyalkylsulphonate, 2-hydroxyalkylthiosulphate such as the products sold by the company Goldschmidt under the names "Abil S201" and "Abil S255", 9—hydroxyacylamino groups, such as the polyorganosiloxanes described in the Application EP-A-342,834.

By way of example there may be mentioned the product Q2 8413 from the company Dow Corning, corresponding to the formula:

mixtures of two PDMSs of different viscosities, such as the product sold by the company General Electric under the name CF 1241, silicones containing hydroxyacylamino groups.

The water-insoluble silicones employed in the compositions in accordance with the invention are present in proportions of betweens 0.2 and 30% and preferably between 0.4 and 15% by weight relative to the total weight of the compositions.

The polymer derived from diallyldialkylammonium and from an anionic monomer which is employed in accordance with the invention is in particular a polymer containing approximately 60 to approximately 99% by weight of units derived from a quaternary diallyldialkylammonium monomer in which the alkyl groups are chosen independently from alkyl groups containing 1 to 18 carbon atoms and in which the anion is derived from an acid which has an ionisation constant higher than $10^{-13}$ and 1 to 40% by weight of this polymer, of an anionic monomer chosen from acrylic or methacrylic acids, the molecular weight of this polymer being between approximately 50,000 and 10,000,000, determined by gel permeation chromatography. Such polymers are described in the Application EP-A-269,243.

The preferred polymers are, among others, the polymers containing alkyl groups chosen from groups containing 1 to 4 carbon atoms and more particularly methyl and ethyl groups.

Among these polymers, those particularly preferred are the copolymers of dimethyldiallylammonium or diethyldiallylammonium chloride and of acrylic acid.

By way of products which are particularly preferred there may be mentioned the polymer sold under the name Merquat 280 by the company Calgon in the form of an aqueous solution containing 35% of active substance, this polymer being a copolymer of diallyldimethylammonium chloride and acrylic acid in proportions of 80/20, the viscosity in the Brookfield LVF module 4 viscometer being between 4,000 and 10,000 cPs, the molecular weight being approximately equal to 1,300,000.

This polymer is employed in proportions by weight relative to the total weight of the composition of between 0.1 and 10% by weight and preferably between 0.5 and 5% by weight relative to the total weight of the composition.

The pH of the compositions is generally between 2 and 9 and more particularly between 3 and 8.

The aqueous medium may consist solely of water or a mixture of water and of a cosmetically acceptable solvent, such as a $C_1$–$C_4$ lower alcohol like ethanol, isopropanol or n-butanol, alkylene glycols like ethylene glycol, and glycol ethers.

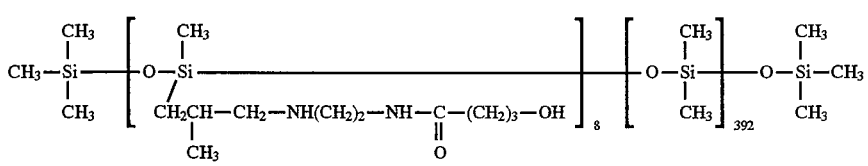

The polyorganosiloxanes which are more particularly preferred, in accordance with the invention, are:

silicone oils of high viscosity of between 0.2 and 2.5 m²/s at 25° C., such as the oils 47 V 500,000 from the company Rhône Poulenc, mixtures of organopolysiloxanes and cyclic silicones, such as the product Q2 1401 sold by the company Dow Corning, The compositions in accordance with the invention may also contain dispersing agents other than alcohols, containing 27 to 44 carbon atoms and containing one or two ether and/or thioether or sulphoxide groups.

Among these agents the following compounds may be mentioned more particularly:

a) RX (III) in which R is an aliphatic radical containing a long carbon chain optionally interrupted by oxygen atoms, and X is a carboxylic, sulphuric or phosphoric acid residue or a radical derived from a carboxylic acid or from an amide.

These compounds of formula (III) are chosen from those in which:
(i) R is a $C_{11}$–$C_{21}$ alkyl or alkenyl radical X is:
a group COOA where A is a mono- or polyhydroxyalkyl radical derived from a $C_2$–$C_3$ polyol or a radical $CH_2CH_2SO_3M$,
a group $CO(OCH_2CH_2)_n$—OH where n has a value of between 2 and 150,
a group

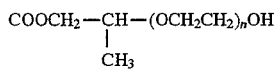

where n has a value of between 2 and 150, it being possible for the free OH functional groups of the groups defined above to be esterified with an acid RCOOH where R is a $C_{11}$–$C_{21}$ alkyl or alkenyl,
a group $CONR_1R_2$ where $R_1$ and $R_2$ denote hydrogen or $C_1$–$C_4$ hydroxyalkyl, at least one denoting $C_1$–$C_4$ hydroxyalkyl,
a group $OSO_3M$ or $\frac{1}{3}$ $PO_4^{3-}M_3$ where M denotes an alkali metal, ammonium or a $C_1$–$C_4$ alkanolamine residue;
(ii) R denotes a radical $R_3(OC_2H_4)_iOCH_2$ and X denotes a group COOM where M has the meaning indicated above, $R_3$ denoting a $C_{12}$–$C_{14}$ alkyl radical and 1 a whole or decimal number between 2.5 and 10, or else $R_3$ denotes oleyl and 1 varies from 2 to 9, or else $R_3$ denotes $C_8$–$C_9$-alkylphenyl and 1 varies from 4 to 8, or the derivatives in which R denotes a $C_{12}$–$C_{16}$ alkyl ether group and X a group $CONR_1R_2$ in which $R_1$ and $R_2$ have the same meaning as that indicated above;
b) oxides of dimethyl-$C_{16}$–$C_{22}$-alkylamines;
c) biopolysaccharides chosen, for example, from xanthan gums and scleroglucanes.

These dispersing agents are employed in compositions in accordance with the invention in proportions of between 0.1 and 20% by weight and preferably between 0.5 and 10% by weight relative to the total weight of the composition.

These compositions may also contain up to 3% of lustering or opacifying agents such as sodium or potassium palmitates, sodium or potassium stearates or hydroxystearates and ethylene glycol mono- or distearate.

The compositions in accordance with the invention may also contain viscosity modifiers such as electrolytes like sodium chloride or sodium xylenesulphonate, hydrotropic agents or thickeners such as cellulose derivatives like, for example, carboxymethyl cellulose, hydroxypropyl cellulose, hydroxyethyl cellulose, guar gum and hydroxypropylated guar gums.

These viscosity modifiers are employed in proportions ranging up to 10% by weight relative to the total weight of the composition and preferably lower than 5%.

The compositions according to the invention may optionally also contain other agents whose effect is to improve the properties of keratinous matter, in particular the cosmetic properties of hair, on condition that they do not impair the stability of the compositions, such as cationic surface-active agents, polymers other than the copolymers of diallyldialkylammonium and of an anionic monomer or proteins or else silicones which are soluble in the mixture.

The polymers, the cationic surfactants, the proteins and the silicones additionally employed in the compositions in accordance with the invention are employed in proportions of between 0.05 and 6% and preferably between 0.1 and 3% by weight relative to the total weight of the composition.

Finally, the compositions according to the invention may contain various adjuvants which are usually employed in washing compositions, such as perfumes, stabilisers, sequestrants, foam stabilisers, propellants, colorants, sunscreens, acidifying or alkalifying agents or other adjuvants depending on the intended use.

The processes of washing and/or conditioning of the keratinous matter and in particular of hair consist in applying a composition as defined above to the latter, this application being followed by a rinsing stage.

The compositions may be employed, inter alia, as shampoos, but also as shower gels for washing hair and the skin, in which case they are applied to wet skin and hair and are rinsed off after application.

The examples which follow are intended to illustrate the invention without, however, being limiting in nature.

EXAMPLE 1

A shampoo of the following composition is prepared:

| | |
|---|---|
| Surfactant of polyoxyethylenated carboxylic ether acid type, of formula: $R(OCH_2CH_2)_nOCH_2COOH$ in which: R = nonylphenol n = mean value of 7 sold under the name Akypo NP 70 by the company Chem Y containing 90% of AS | 10.0 g AS |
| triethanolamine lauryl sulphate containing 40% of AS | 10.0 g AS |
| copolymer of diallyldimethylammonium chloride and acrylic acid, sold under the name Merquat 280 by the company Calgon, containing 35% of AS | 1.0 g AS |
| polyphenylmethylsiloxane sold under the name Silbione Huile 70633 V 30 by the company Rhône Poulenc | 2.5 g |
| copra acid diethanolamide | 2.5 g |
| sodium chloride | 4.0 g |
| triethanolamine q.s. pH = 7.5 | |
| perfume, stabilisers q.s. | |
| water   q.s. | 100 g |

EXAMPLE 2

A shampoo of the following composition is prepared:

| | |
|---|---|
| Surfactant of polyoxyethylenated carboxylic ether acid type, of formula: $R(OCH_2CH_2)_nOCH_2COOH$ in which: R = octylphenyl n = mean value of 4 sold under the name Akypo OP 40 by the company Chem Y containing 90% of AS | 8.0 g AS |
| ammonium lauryl sulphate containing 30% of AS | 6.0 g AS |
| sodium α-olefinsulphonate containing 38% of AS | 6.0 g AS |
| polydimethylsiloxane sold under the name Silbione Huile 47 V 500,000 by the company Rhône Poulenc | 2.0 g |
| copolymer of diallyldimethylammonium chloride and acrylic acid, sold under the name Merquat 280 by the company Calgon, containing 35% of AS | 0.3 g AS |
| sodium chloride | 4.0 g |
| sodium hydroxide q.s. pH = 4.4 | |
| perfume, stabilisers q.s | |
| water   q.s. | 100 g |

EXAMPLE 3

A shampoo of the following composition is prepared:

| | |
|---|---|
| surfactant of polyoxyethylenated carboxylic ether acid type, of formula: R(OCH$_2$CH$_2$)$_n$OCH$_2$COOH in which: R = C$_{12}$–C$_{14}$ alkyl n = mean value of 2.5 sold under the name Akypo RLM 25 by the company Chem Y, containing 90% of AS | 5.0 g AS |
| triethanolamine lauryl sulphate containing 40% of AS | 10.0 g AS |
| cocoylbetaine containing 32% of AS | 2.0 g AS |
| copolymer of diallyldimethylammonium chloride and acrylic acid, sold under the name Merquat 280 by the company Calgon, containing 35% of AS | 2.0 g AS |
| mixture of two PDMSs of different viscosities, sold under the name CF 1241 by the company General Electric | 3.0 g |
| scleroglucan sold at a concentration of 90% of AS under the name Actigum CS 11 by the company Sanofi Bio Industrie | 0.9 g AS |
| sodium chloride | 3.0 g |
| triethanolamine q.s. pH = 6 perfume, stabilisers q.s | |
| water   q.s. | 100 g |

EXAMPLE 4

A shampoo of the following composition prepared:

| | |
|---|---|
| oxyethylenated sodium lauryl ether sulphate containing 2 moles of ethylene oxide, containing 28% of AS | 12.0 g AS |
| cocoylbetaine containing 32% of AS | 1.5 g AS |
| ethylene glycol distearate | 2.0 g AS |
| copra acid diethanolamide | 1.5 g |
| copolymer of diallyldimethylammonium chloride and acrylic acid, sold under the name Merquat 280 by the company Calgon, containing 35% of AS | 0.5 g AS |
| mixture of two PDMSs of different viscosities, sold under the name CF 1241 by the company General Electric | 2.5 g |
| triethanolamine q.s. pH = 6.8 perfume, stabilisers, q.s. | |
| water   q.s. | 100 g |

EXAMPLE 5

A shampoo of the following composition is prepared:

| | |
|---|---|
| sodium lauryl sulphate containing 85% of AS | 30.0 g AS |
| sodium lauroylsarcosinate containing 30% of AS | 4.0 g AS |
| polydimethylsiloxane sold under the name Silbione Huile 47 V 500,000 by the company Rhône Poulenc | 3.0 g |
| copolymer of diallyldimethylammonium chloride and acrylic acid, sold under the name Merquat 280 by the company Calgon, containing 35% of AS | 2.0 g AS |
| lauric acid diethanolamide | 2.0 g |
| copra acid monoethanolamide | 2.0 g |
| PEG 150 distearate | 0.4 g |
| sequestrant | 0.2 g |
| citric acid   q.s.   pH = 6.5 | |
| water   q.s. | 100 g |

EXAMPLE 6

A shampoo of the following composition is prepared:

| | |
|---|---|
| surfactant of polyoxyethylenated carboxylic ether acid type, of formula: R(OCH$_2$CH$_2$)$_n$OCH$_2$COOH in which: R = nonylphenyl n = mean value of 7 sold under the name Akypo NP 70 by the company Chem Y, containing 90% of AS | 10.0 g AS |
| triethanolamine lauryl sulphate, containing 40% of AS | 10.0 g AS |
| copolymer of diallyldimethylammonium chloride and acrylic acid, sold under the name Merquat 280 by the company Calgon, containing 35% of AS | 1.0 g AS |
| polyorganosiloxane containing hydroxy-acylamino groups, sold under the name Q2 8413 by the company Dow Corning | 2.5 g |
| copra acid diethanolamide | 2.5 g |
| sodium chloride | 3.0 g |
| triethanolamine q.s pH = 7.5 perfume, stabilisers   q.s. | |
| water   q.s. | 100 g |

EXAMPLE 7

A shower gel of the following composition is prepared:

| | |
|---|---|
| sodium lauryl (70/30 C$_{12}$–C$_{14}$) ether sulphate oxyethylenated with 2.2 moles of ethylene oxide, sold at a concentration of 28% of AS | 22.4 g AS |
| 25/5 mixture of cocoylamidopropylbetaine and of glycerol monolaurate in aqueous solution containing 30% of AS, sold under the name Tegobetaine HS by the company Goldschmidt | 2.58 g AS |
| polydimethylsiloxane (MW 250,000) sold under the name Silbione 70047 V 500,000 by the company Rhône Poulenc | 2.0 g |
| copolymer of diallyldimethylammonium chloride and acrylic acid, sold under the name Merquat 280 by the company Calgon, containing 35% of AS | 0.5 g AS |
| ethylene glycol distearate (70/30 C$_{16}$–C$_{18}$) | 2.0 g |
| triethanolamine   q.s.   pH = 7 perfume, stabilisers   q.s. | |
| water   q.s. | 100.0 g |

We claim:

1. A composition for washing or conditioning keratinous matter consisting essentially of an aqueous medium, 5 to 50% by weight relative to the total weight of the composition of a surface-active agent possessing detergent properties, 0.2 to 30% by weight relative to the total weight of the composition of at least one silicone which is insoluble in the medium and 0.1 to 10% by weight relative to the total weight of the composition of at least one amphoteric copolymer derived from diallyldialkylammonium and an anionic monomer which contains 60 to 99% by weight of units derived from a quaternary diallyldialkylammonium monomer in which the alkyl groups have, independently from each other, 1 to 18 carbon atoms, the corresponding anion being derived from an acid which has an ionization constant higher than $10^{-13}$ and approximately 1 to 40% by weight of units of an anionic monomer selected from the group consisting of acrylic acid and methacrylic acid, having a molecular weight between 50,000 and 10,000,000 determined by gel permeation chromatography, wherein said composition does not contain an alcohol dispersing agent containing 27 to 44 carbon atoms and containing a functional group selected from the group consisting of an ether group, a thioether group and a sulphoxide group.

2. The composition according to claim 1 in which the silicone is a polyorganosiloxane which is insoluble in the aqueous medium and is in the form of oil, wax, gum or resin.

3. The composition according to claim 2 in which the polyorganosiloxane is a non-volatile silicone selected from the group consisting of a polyalkylsiloxane, a polyalkylarylsiloxane, a polyarylsiloxane, a silicone gum, a silicon resin, an organomodified polysiloxane and mixtures thereof.

4. The composition according to claim 3 in which the polyalkylsiloxane is selected from the group consisting of a linear polydimethylsiloxane containing trimethylsilyl end groups with a viscosity between $5\times10^{-6}$ and $2.5$ m$^2$/s at $25°$ C., a linear polydimethylsiloxane containing dimethylsilanol end groups and a poly-$C_1$–$C_{20}$-alkylsiloxane.

5. The composition according to claim 2 in which the polyorganosiloxane is selected from the group consisting of a linear polyalkylsiloxane containing a trimethylsilyl end group with a viscosity of between $0.2$ and $2.5$ m$^2$/s at $25°$ C. a mixture of a polydimethylsiloxanes hydroxylated at the end of a chain and a cyclic polydimethylsiloxane, a mixture of two polydimethylsiloxanes consisting of a gum and an oil of different viscosities and a polyorganosiloxane modified with a hydroxyacylamino group.

6. The composition according to claim 1 in which the alkyl groups have between 1 and 4 carbon atoms.

7. The composition according to claim 1 in which the copolymer is derived from dimethyldiallylammonium or diethyldiallylammonium chloride and acrylic acid.

8. The composition according to claim 1 in which the surface-active agent is selected from the group consisting of anionic, amphoteric, zwitterionic and nonionic surface-active agents and mixtures thereof.

9. The composition according to claim 8, wherein
the anionic surface-active agent is selected from the group consisting of alkali metal salts, ammonium salts, amine salts, aminoalcohol salts and magnesium salts of the following compounds: alkyl ether sulphates, alkylamidoether sulphates, alkylarylpolyether sulphates, monoglyceride sulphates, alkylsulphonates, alkylamide sulphonates, alkylarylsulphonates, olefin sulphonates, paraffin sulphonates, alkyl sulphosuccinates,alkyl ether sulphosuccinates, alkylamide sulphosuccinates, alkylsulphosuccinamates, alkyl sulphoacetates, alkyl ether phosphates, acylsarcosinates and N-acyltaurates, in which the alkyl or acyl radical is a carbon chain containing between 12 and 20 carbon atoms; salts of oleic, ricinoleic, palmitic and stearic acids; copra oil and hydrogenated copra oil acids; and acyllactylates in which the acyl radical contains from 8 to 20 carbon atoms;
the nonionic surface-active agent is selected from the group consisting of polyethoxylated, polypropoxylated and polyglycerolated alcohols, alpha-diols and alkylphenols with a fatty acid chain containing between 8 and 18 carbon atoms, the number of ethylene oxide and propylene oxide groups being between 2 and 50 and the number of glycerol groups being between 2 and 30; copolymers of ethylene and propylene oxides; condensates of ethylene and propylene oxides with fatty alcohols; polyethoxylated fatty amides containing 2 to 30 moles of ethylene oxide; polyglycerolated fatty amides containing 1 to 5 glycerol groups; polyethoxylated fatty amines containing 2 to 30 moles of ethylene oxide; oxyethylenated sorbitan fatty acid esters containing 2 to 30 moles of ethylene oxide; sucrose fatty acid esters; alkylpolyglycosides; $C_{10}$–$C_{14}$-alkylamine oxides and N-acylamidopropylmorpholine oxides; and the amphoteric and zwitterionic surface-active agents are selected from the group consisting of derivatives of aliphatic secondary or tertiary amines in which the aliphatic radical is a linear or branched chain containing 8 to 18 carbon atoms and which contains at least one water-solubilizing carboxylate, sulphonate, sulphate, phosphate or phosphonate anionic group; $C_8$–$C_{20}$-alkylbetaines, sulphobetaines, $C_8$–$C_{20}$-alkylamido-$C_1$–$C_6$-alkylbetaines or $C_8$–$C_{20}$-alkylamido-$C_1$–$C_5$-alkylbetaines.

10. The composition according to claim 9 in which the composition also contains a dispersing agent having the formula RX in an amount between 0.1 and 20% by weight of the total weight of the composition, selected from the group consisting of
(i) RX compounds in which R is a $C_{11}$–$C_{21}$ alkyl or alkenyl radical and X is selected from the group consisting of
(a) COOA where A is a mono- or polyhydroxyalkyl radical derived from a $C_2$–$C_3$ polyol or a radical $CH_2CH_2SO_3M$ where M is an alkali metal, ammonium or a $C_1$–$C_4$alkanolamine residue;
(b) $CO(OCH_2CH_2)_n$—OH where n has a value of between 2 and 150;
(c)

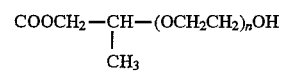

where n has a value of between 2 and 150;
(d) $CONR_1R_2$ where $R_1$ and $R_2$ are hydrogen or $C_1$–$C_4$ hydroxyalkyl with at least one being $C_1$–$C_4$ hydroxyalkyl; and
(e) $OSO_3M$ or $\frac{1}{3}$ $PO_4M_3$ where M is an alkali metal, ammonium or a $C_1$–$C_4$ alkanolamine residue;
(ii) RX compounds which are esters formed by the reaction of R, where R is a $C_{11}$–$C_{21}$ alkyl or alkenyl radical and X is selected from the group consisting of:
(a) COOA where A is a mono- or polyhydroxyalkyl radical derived from a $C_2$–$C_3$ polyol or a radical $CH_2CH_2SO_3M$ where M is an alkali metal, ammonium or a $C_1$–$C_4$ alkanolamine residue;
(b) $CO(OCH_2CH_2)_n$—OH where n has a value of between 2 and 150; and
(c)

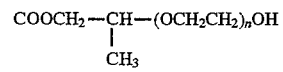

where n has a value of between 2 and 150; and
(iii) RX compounds in which R is a radical $R_3(OC_2H_4)_i OCH_2$ selected from the group consisting of
(a) $R_3(OC_2H_4)_iOCH_2$ compounds in which $R_3$ is a $C_{12}$–$C_{14}$ alkyl radical and i is a whole or decimal number between 2.5 and 10;
(b) $R_3(OC_2H_4)_iOCH_2$ compounds in which $R_3$ is an oleyl and i is a whole decimal number between 2 to 9; and
(c) $R_3(OC_2H_4)_iOCH_2$ compounds in which $R_3$ is a $C_8$–$C_9$ alkylphenyl and i is a whole or decimal number between 4 to 8;

and X is COOM, where M is selected from the group consisting of an alkali metal, an ammonium group and a $C_1$-$C_4$alkanolamine residue.

11. The composition according to claim 1 in which the aqueous medium is water or a mixture of water and a cosmetically acceptable solvent in which the cosmetically acceptable solvent is selected from the group consisting of a $C_1$-$C_4$ lower alcohol, an alkylene glycol, a glycol ether, and mixtures thereof.

12. The composition according to claim 1 in which the composition also contains a lustering or opacifying agent present in proportions ranging up to 3% by weight relative to the total weight of the composition.

13. The composition according to claim 1 in which the composition also contains a viscosity modifier selected from the group consisting of an electrolyte, a hydrotropic agent and a thickening agent; said modifier being present in proportions ranging up to 10% by weight relative to the total weight of the composition.

14. The composition according to claim 1 in which the composition also contains an agent to improve the cosmetic properties of hair or skin selected from the group consisting of a cationic surface-active agent, a polymer other than the copolymer derived from diallyldialkylammonium and an anionic monomer, a protein and a silicone which is soluble in the composition.

15. A process for washing or conditioning keratinous matter consisting essentially of applying a composition which comprises an aqueous medium, 5 to 50% by weight relative to the total weight of the composition of a surface-active agent possessing detergent properties, 0.2 to 30% by weight relative to the total weight of the composition of at least one silicone which is insoluble in the medium and 0.1 to 10% by weight relative to the total weight of the composition of at least one amphoteric copolymer derived from diallyldialkylammonium and an anionic monomer which contains 60 to 99% by weight of units derived from a quaternary diallyldialkylammonium monomer in which the alkyl groups have, independently from each other, 1 to 18 carbon atoms, the corresponding anion being derived from an acid which has an ionization constant higher than $10^{-13}$ and approximately 1 to 40% by weight of units of an anionic monomer selected from the group consisting of acrylic acid and methacrylic acid, having a molecular weight between 50,000 and 10,000,000 determined by gel permeation chromatography, wherein said composition does not contain an alcohol dispersing agent containing 27 to 44 carbon atoms and containing a functional group selected from the group consisting of an ether group, a thioether group and a sulphoxide group.

16. A composition for washing or conditioning keratinous matter consisting essentially of an aqueous medium, 5 to 50% by weight relative to the total weight of the composition of a surface-active agent possessing detergent properties, 0.2 to 30% by weight relative to the total weight of the composition of at least one polyalkylsiloxane which is insoluble in the medium and 0.1 to 10% by weight relative to the total Weight of the composition of at least one amphoteric copolymer derived from diallyldialkylammonium and an anionic monomer which contains 60 to 99% by weight of units derived from a quaternary diallyldialkylammonium monomer in which the alkyl groups have, independently from each other, 1 to 18 carbon atoms, the corresponding anion being derived from an acid which has an ionization constant higher than $10^{-13}$ and approximately 1 to 40% by weight of units of an anionic monomer selected from the group consisting of acrylic acid and methacrylic acid, having a molecular weight between 50,000 and 10,000,000 determined by gel permeation chromatography, wherein said composition does not contain an alcohol dispersing agent containing 27 to 44 carbon atoms and containing a functional group selected from the group consisting of an ether group, a thioether group and a sulphoxide group.

17. The composition according to claim 16 in which the composition further consists essentially of a dispersing agent having a formula RX, selected from the group consisting of (i) RX compounds in which R is a $C_{11}$-$C_{21}$ alkyl or alkenyl radical and X is selected from the group consisting of
  (a) COOA where A is a mono- or polyhydroxyalkyl radical derived from a $C_2$-$C_3$ polyol or a radical $CH_2CH_2SO_3M$ where M is an alkali metal, ammonium or a $C_1$-$C_4$ alkanolamine residue;
  (b) $CO(OCH_2CH_2)_n$—OH where n has a value of between 2 and 150;
  (c)

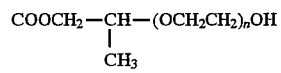

where n has a value of between 2 and 150;
  (d) $CONR_1R_2$ where $R_1$ and $R_2$ are hydrogen or $C_1$-$C_4$ hydroxyalkyl with at least one being $C_1$-$C_4$hydroxyalkyl; and
  (e) $OSO_3M$ or $\frac{1}{3} PO_4M_3$ where M is an alkali metal, ammonium or a $C_1$-$C_4$ alkanolamine residue;

(ii) RX compounds which are esters formed by the reaction of R, where R is a $C_{11}$-$C_{21}$ alkyl or alkenyl radical and X is selected from the group consisting of:
  (a) COOA where A is a mono- or polyhydroxyalkyl radical derived from a $C_2$-$C_3$ polyol or a radical $CH_2CH_2SO_3M$ where M is an alkali metal, ammonium or a $C_1$-$C_4$ alkanolamine residue;
  (b) $CO(OCH_2CH_2)_n$—OH where n has a value of between 2 and 150; and
  (c)

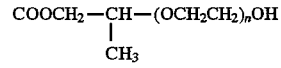

where n has a value of between 2 and 150; and (iii) RX compounds in which R is a radical $R_3(OC_2H_4)_i OCH_2$ selected from the group consisting of
  (a) $R_3(OC_2H_4)_iOCH_2$ compounds in which $R_3$ is a $C_{12}$-$C_{14}$ alkyl radical and i is a whole or decimal number between 2.5 and 10;
  (b) $R_3(OC_2H_4)_iOCH_2$ compounds in which $R_3$ is an oleyl and i is a whole decimal number between 2 to 9; and
  (c) $R_3(OC_2H_4)_iOCH_2$ compounds in which $R_3$ is a $C_8$-$C_9$ alkylphenyl and i is a whole or decimal number between 4 to 8;

and X is COOM, where M is selected from the group consisting of an alkali metal, an ammonium group and a $C_1$-$C_4$ alkanolamine residue, and in which the surface active agent is selected from a group consisting of (i) an anionic surface-active agent selected from the group consisting of alkali metal salts, ammonium salts, amine salts, aminoalcohol salts and magnesium salts of the following compounds: alkyl ether sulphates, alkylamidoether sulphates, alkylarylpolyether sulphates, monoglyceride sulphates, alkylsulphonates, alkylamide sulphonates, alkylarylsulphonates, olefin sulphonates, paraffin sulphonates, alkyl sulphosuccinates, alkyl ether sulphosuccinates, alkylamidesulphosuccinates, alkylsulphosuccinamates, alkylsulphoacetates, alkyl ether phosphates, acylsarcosinates and N-acyltaurates, in which the alkyl or acyl radical is a carbon chain containing between 12 and 20 carbon atoms; salts of oleic, ricinoleic, palmitic and stearic acids; copra oil and hydrogenated copra oil acids; and acyl-lactylates in which the acyl radical contains from 8 to 20 carbon atoms; (ii) a nonionic surface-active agent selected from the group consisting of polyethoxylated, polypropoxylated and polyglycerolated alcohols, alpha-diols and alkylphenols with a fatty acid chain containing between 8 and 18 carbon atoms, the number of ethylene oxide and propylene oxide groups being between 2 and 50 and the number of glycerol groups being between 2 and 30; copolymers of ethylene and propylene oxides; condensates of ethylene and propylene oxides with fatty alcohols; polyethoxylated fatty amides containing 2 to 30 moles of ethylene oxide; polyglycerolated fatty amides containing 1 to 5 glycerol groups; polyethoxylated fatty amines containing 2 to 30 moles of ethylene oxide; oxyethlenated sorbitan fatty acid esters containing 2 to 30 moles of ethylene oxide; sucrose fatty acid esters; alkylpolyglycosides; $C_{10}$–$C_{14}$-alkylamine oxides and N-acylamidopropylmorpholine oxides; and (iii) amphoteric and zwitterionic surface-active agents selected from the group consisting of derivatives of aliphatic secondary or tertiary amines in which the aliphatic radical is a linear or branched chain containing 8 to 18 carbon atoms and which contains at least one water-solubilizing carboxylate, sulphonate, sulphate, phosphate or phosphonate anionic group; $C_8$–$C_{20}$-alkylbetaines, sulphobetaines, $C_8$–$C_{20}$-alkylamido-$C_1$–$C_6$-alkylbetaines or $C_8$–$C_{20}$-alkylamido-$C_1$–$C_5$-alkylbetaines.

* * * * *

UNITED STATES PATENT AND TRADEMARK OFFICE
CERTIFICATE OF CORRECTION

PATENT NO. : 5,650,383

DATED : July 22, 1997

INVENTOR(S) : Dubief et al.

It is certified that error appears in the above-identified patent and that said Letters Patent is hereby corrected as shown below:

Column 5, line 37, "artionic" should read --anionic--;

Column 7, line 5, "X is" should appear on a separate line;

Column 9, line 30, "prepared" should read --is prepared--;

Column 9, line 36, "2.0 g AS" should read --2.0 g--;

Column 13, lines 28-29, "consisting essentially of applying a compositoon which comprises" should read --which comprises applying a composition consisting essentially of--;

Column 13, line 58, "Weight" should read --weight--.

Signed and Sealed this

Thirty-first Day of March, 1998

*Attest:*

BRUCE LEHMAN

*Attesting Officer*     *Commissioner of Patents and Trademarks*